United States Patent [19]

Kuhla et al.

[11] 4,132,847

[45] Jan. 2, 1979

[54] 4-PYRONE PROSTAGLANDIN ANTAGONISTS

[75] Inventors: Donald E. Kuhla, Gales Ferry; Jacob J. Plattner, East Lyme, both of Conn.

[73] Assignee: Pfizer Inc., New York, N.Y.

[21] Appl. No.: 818,043

[22] Filed: Jul. 22, 1977

[51] Int. Cl.$^2$ .................. C07D 309/22; A61K 31/35
[52] U.S. Cl. ............................. 542/441; 260/345.7 P; 260/345.8 P; 424/283
[58] Field of Search ................. 260/345.7 R, 345.8 R, 260/345.7 P, 345.8 P; 542/441

[56]  References Cited

U.S. PATENT DOCUMENTS 3,468,916  9/1969  Tate et al. ...................... 260/345.9 R

OTHER PUBLICATIONS

Sanner, Arch. Intern. Med., 133, 133 (1974).
Bennett, Advances in Drug Research, 8, 83, (1974).

*Primary Examiner*—Nicky Chan
*Attorney, Agent, or Firm*—Francis X. Murphy; Charles J. Knuth; Peter C. Richardson

[57]  ABSTRACT

Novel 2,3,6-substituted-4-pyrones having activity as prostaglandin antagonists are disclosed, together with intermediates useful for the preparation thereof. Methods of using the compounds of this invention as prostaglandin antagonists are described.

12 Claims, No Drawings

4-PYRONE PROSTAGLANDIN ANTAGONISTS

BACKGROUND OF THE INVENTION

This invention relates to 2,3,6-substituted-4-pyrone derivatives having prostaglandin antagonist activity and to intermediates useful in the preparation of such 4-pyrones. Methods of using these compounds are also disclosed.

Prostaglandin antagonists are those compounds which selectively inhibit the action of prostaglandins at their site of action. Relatively few compounds are known which have utility in this respect, those that are known mainly belonging to three chemically unrelated classes, dibenzoxepine derivatives, polyphloretin phosphates and 7-oxaprostaglandins. These and other known prostaglandin antagonists are reviewed by Sanner, Arch. Intern. Med. 133, 133 (1974) and by Bennett, Advances in Drug Research, 8, 83 (1974).

Prostaglandins have been associated with a number of diseases or undesirable conditions. For example, an increased physiological availability of prostaglandins may be associated with pain, inflammation, diarrhea, habitual labor, hypertension, glaucoma, sickle-cell anemia and other such conditions. Prostaglandin antagonists offer a method of treating and alleviating such undesirable conditions by inhibiting the action of the responsible prostaglandin at the site of action.

SUMMARY OF THE INVENTION

The present invention relates to novel prostaglandin antagonists which are 2,3,6-substituted-4-pyrones of the formula

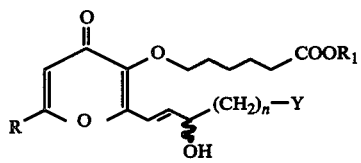

I wherein
 $R_1$ is hydrogen or alkyl of 1 to 6 carbon atoms;
 R is selected from hydrogen, methyl, ethyl, n-propyl and 1-hydroxyalkyl, wherein said alkyl is methyl, ethyl and n-propyl;
 Y is selected from methyl, phenyl and monosubstituted phenyl, wherein said substituent is methyl, methoxy, chloro or fluoro; and
 n is an integer from 1 to 4; and
 the pharmaceutically acceptable salts of said compounds wherein $R_1$ is hydrogen.

Preferably, the group R is selected from hydrogen, methyl and hydroxymethyl and preferably the group Y is selected from methyl and phenyl. Especially preferred are compounds where R is hydrogen, including the compound wherein $R_1$ is ethyl, n is 4 and Y is methyl and the compound wherein $R_1$ is ethyl, n is 2 and Y is phenyl. Of the preferred compounds where R is methyl, especially preferred is the compound wherein $R_1$ is ethyl, n is 4 and Y is methyl. Of the preferred compounds where R is hydroxymethyl, especially preferred is the compound wherein $R_1$ is methyl, n is 4 and Y is methyl.

Intermediates useful for the preparation of the 4-pyrone derivatives of the present invention are those having the formula

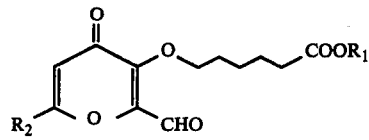

wherein
 $R_1$ is hydrogen or alkyl of 1 to 6 carbon atoms; and $R_2$ is selected from hydrogen, methyl, ethyl, n-propyl and

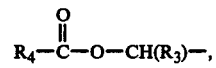

wherein $R_3$ is selected from hydrogen, methyl and ethyl and
 $R_4$ is selected from alkyl of 1 to 4 carbon atoms or phenyl.

Preferred intermediates of this formula are those useful for preparing the preferred 2,3,6-substituted-4-pyrones of formula I described above herein, for example, those intermediates where $R_2$ is hydrogen, methyl or

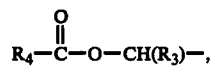

where $R_4$ is alkyl of 1 to 4 carbon atoms.

Further intermediates useful for the preparation of the 4-pyrone derivatives of the present invention are those having the formula

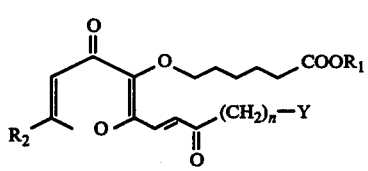

wherein
 $R_1$ is hydrogen, alkyl of 1 to 6 carbon atoms; and $R_2$ is selected from hydrogen, methyl, ethyl, n-propyl and

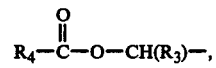

wherein $R_3$ is selected from hydrogen, methyl and ethyl and $R_4$ is selected from alkyl of 1 to 4 carbon atoms or phenyl;
 Y is selected from methyl, phenyl and monosubstituted phenyl wherein said substituent is methyl, methoxy, chloro or fluoro; and
 n is an integer from 1 to 4.

Preferred intermediates are those useful for preparing the preferred 2,3,6-substituted-4-pyrones of formula I described above herein, for example, those intermediates where $R_2$ is hydrogen, methyl or

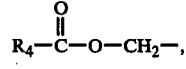

wherein $R_4$ is alkyl of 1 to 4 carbon atoms.

Also disclosed is a method of treating an undesired condition resulting from an abnormally increased physiological availability of prostaglandins of the PGE$_2$ series in an animal, which comprises administering to said animal a compound of formula I in an amount effective to alleviate said undesired condition.

DETAILED DESCRIPTION OF THE INVENTION

Compounds of formula I wherein R is hydrogen, methyl, ethyl or n-propyl may be conveniently prepared by the reaction sequence shown in Scheme A.

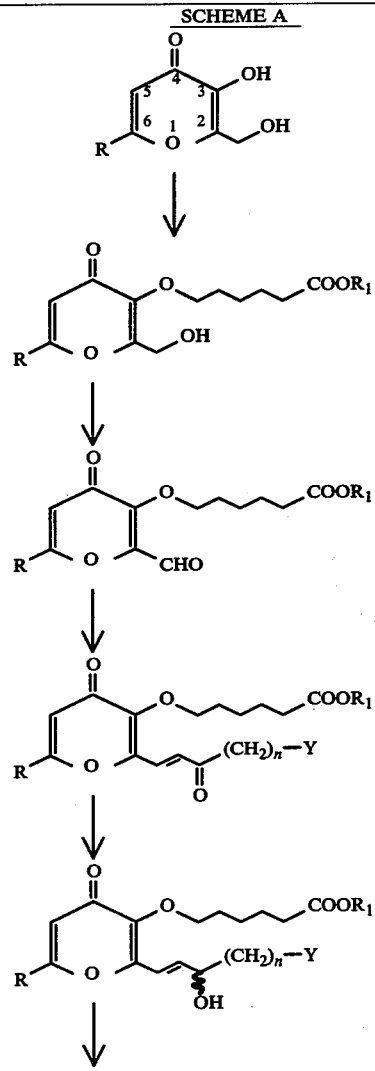

SCHEME A

When R is hydrogen, the starting material is 1 is 2-hydroxymethyl-3-hydroxy-4-pyrone, the preparation of which is described in U.S. Pat. No. 3,130,204. When R is alkyl the corresponding 6-alkyl-substituted compounds are employed. These compounds are known in the art and can also be readily prepared from the analogous 6-(1-hydroxyalkyl)-substituted-4-pyrones described in U.S. Pat. No. 3,468,915 by methods known in the art. The numbering system of the 4-pyrone ring employed throughout the specification is shown in compound 1 in Scheme A. Conversion of these starting materials to compound 2 is effected by reaction with a suitable 6-halohexanoate, X—(CH$_2$)$_5$—COOR$_1$, wherein X is halo and R$_1$ is hydrogen or alkyl of 1 to 6 carbon atoms. The 6-iodo ester is preferred in this reaction. This may, for example, be conveniently generated in situ by using the 6-bromo-hexanoate and potassium or sodium iodide. The reaction is generally conducted in the presence of a base such as potassium or sodium hydroxide in an alcohol-water solution. Preferably the alcohol employed as solvent is of the formula R$_1$OH wherein R$_1$ is as defined above. The reaction is conducted at between about 50° C. and 150° C., preferably at reflux temperatures and preferably in an inert atmosphere, such as nitrogen. The desired intermediate 2 can be isolated by removal of the alcohol solvent. The hydroxy-methyl group at the 2- position of compound 2 is converted to formyl to form compound 3 by reaction with manganese dioxide or other suitable reagents for the oxidation of allylic alcohols. The reaction with manganese dioxide is conducted at a temperature from about −20° C. to about 50° C., preferably at about room temperature in a suitable organic solvent such as acetone, chloroform, acetonitrile or methylene chloride. The reaction time will vary with the temperature employed, but will usually be from about 30 minutes to about 4 hours. Other suitable oxidation agents are known in the art, for example, those described by Pfitzner and Moffatt, J.A.C.S. 85, 3027 (1963) and these may be employed for preparing the useful intermediates 3 for preparation of the prostaglandin antagonists of the present invention. The aldehyde 3 may be purified and isolated if desired by removal of excess solvent and recrystallization or by chromatography. The aldehyde 3 is then reacted with a ketophosphonate, generally prepared by condensation of the appropriate ester with a dialkyl methylphosphonate, see Corey et al, J.A.C.S. 90, 3247 (1968). The particular ketophosphonate employed will vary according to the length of the side chain desired at the 2-position of the pyrone ring and with the terminal group Y of that chain. Reaction of the aldehyde 3 and the ketophosphonate is generally conducted in an inert organic solvent, usually an ether such as tetrahydrofuran or 1,2-dimethoxyethane, in the presence of an alkali metal hydride, preferably sodium hydride, or n-butyl lithium. The reaction is preferably conducted at about room temperature. Compound 4 is then reacted with a reducing agent to convert the keto group of the 2- substituent side chain to hydroxyl, forming the desired prostaglandin antagonists of formula I. This may be effected by the use of an alkali metal trialkylborohydride, such as a potassium, sodium or lithium trialkylborohydride wherein each alkyl group is of 1 to 4 carbon atoms. A preferred reagent is lithium triethylborohydride. The reaction is conducted in an inert organic solvent, generally an ether such as, but not limited to, tetrahydrofuran, diethyl ether or 1,2-dimethoxyethane at a temperature below about −10° C., preferably between about −50° C. to about −90° C. The reaction may also be effected with zinc borohydride at temperatures between about 10° C. and about 50° C., preferably at room temperature, in a suitable organic solvent, usually an ether such as but not limited to tetrahydrofuran, diethyl ether or 1,2-dimethoxyethane. The reduction may also be effected with sodium borohydride in an alkyl alcohol solvent having from 1 to 4 carbon atoms, preferably ethanol or methanol, at temperatures from about −10° C. to about −30° C.

The reactions described above are also used to form the compounds of the present invention where the group R is 1-hydroxyalkyl, wherein alkyl is methyl, ethyl and n-propyl, from the appropriate 2-hydroxymethyl-3-hydroxy-6-(1-hydroxyalkyl)-4-pyrones, which are described in U.S. Pat. No. 3,468,915. However, before following the above described reaction sequence it is necessary to protect the 1-hydroxy group of the 6-substitutent of the pyrone ring. The reaction sequence for the formation of compounds of formula I wherein R is 1-hydroxyalkyl is represented in Scheme B.

dehyde or substituted benzaldehyde. A convenient method of forming the protected compound 7 in good yield is by the reaction of the starting material 6 with benzaldehyde diethylacetal. The reaction is conducted in the presence of a strong acid catalyst, such as hydrochloric acid, sulfuric acid, p-toluenesulfonic acid or sulfonic ion-exchange resins. This reaction is generally conducted in a suitable organic solvent, such as dimethyl sulfoxide or dimethylformamide at a temperature of about 60° to 120° C. The conversion of compund 7 to compound 8 is effected by the reaction of the remaining hydroxyl group with a carboxylic acid halide,

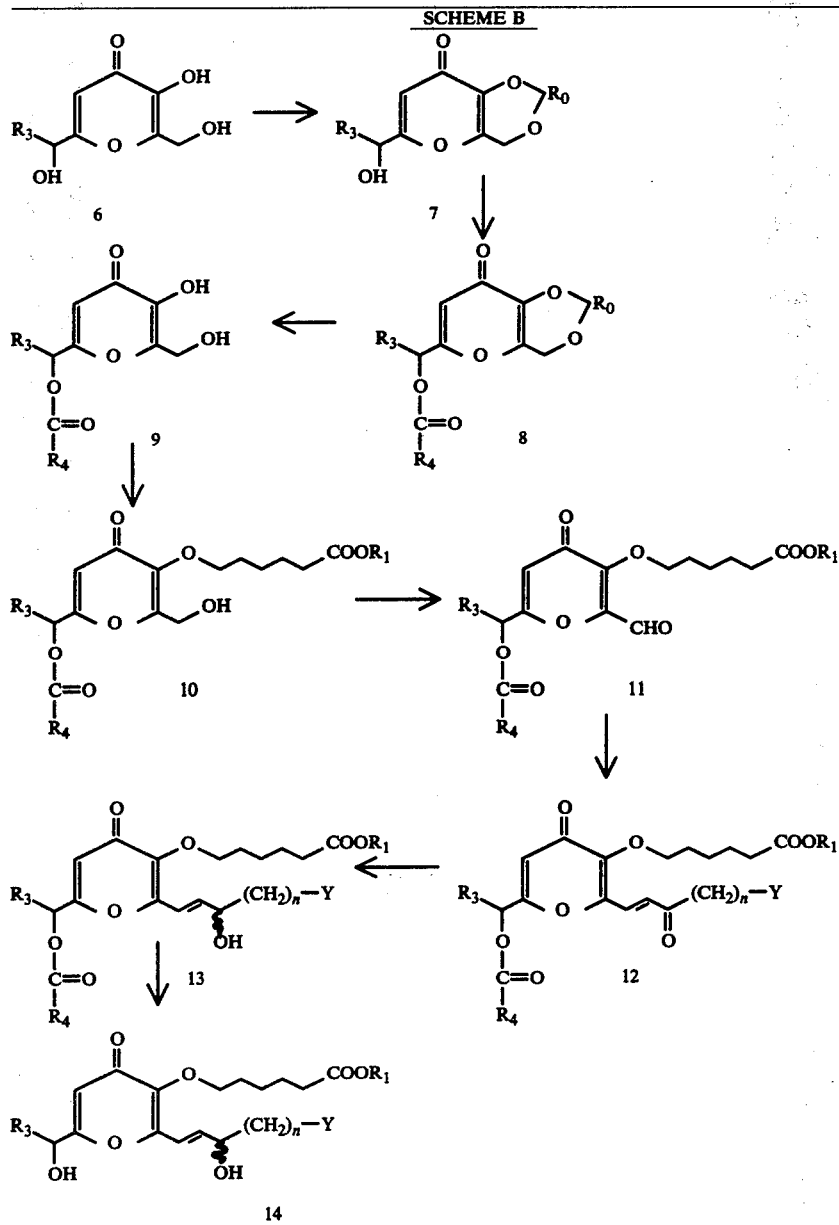

SCHEME B $R_1$, $R_3$, $R_4$, Y and n are as previously defined and $R_0$ is an acid-labile difunctional hydroxyl-protecting group effective to react with the hydroxyl groups at the 3-position and the hydroxymethyl at the 2-position of the pyrone ring. The first step of the reaction sequence is preferably effected by formation of an acetal, particularly preferred acetals being those derived from benzalpreferably the acid chloride, or a carboxylic acid anhydride. Preferred protecting groups are those wherein $R_4$ is alkyl of 1 to 4 carbon atoms or phenyl. Especially preferred are those compounds wherein $R_4$ is t-butyl. However, any compound forming an ester which will protect the hydroxyl group during the reaction sequence and can be subsequently removed at the end of the reaction sequence may be employed. The next step is the regeneration of the hydroxyl groups at the 3-position and on the 2- substituent of the pyrone ring to form compound 9. This may be achieved by acid hydrolysis using, for example, a carboxylic acid-water mixture, such as about 65% acetic acid in water and heating from about 50° C. to about 100° C. until hydrolysis is substantially complete, usually about 1 to 4 hours depending on the temperature employed. Compound 9 is then reacted with a 6-halo hexanoate to form compound 10, which is oxidized to 11 by manganese dioxide or other suitable oxidizing agents effective to convert an allylic alcohol to formyl. The aldehyde 11 is reacted with a ketophosphonate to form the extended side chain at the 2- position of the pyrone ring, followed by reduction of the keto group to hydroxyl with zinc borohydride, an alkali metal trialkylborohydride, or sodium borohydride. The conditions and suitable reagents for preparation of compounds 10 through 13 are as previously described for the corresponding steps of reaction scheme A. The final step is to remove the protecting group and reform the 1-hydroxyalkyl group at the 6- position of the 4-pyrone ring.

This may be effected by hydrolysis in the presence of a base, such as an alkali metal hydroxide, alkoxide or carbonate, the sodium and potassium compounds generally being preferred. The reaction may be conducted in a hydroxylic solvent such as alkyl alcohol having 1 to 4 carbon atoms or in alcohol-water mixtures at temperatures between about 0° C. and 50° C.

The compounds of formula I wherein $R_1$ is alkyl of 1 to 6 carbon atoms may, if desired, be prepared from the corresponding compounds wherein $R_1$ is hydrogen by any means known in the art for conversion of an acid to an ester. Thus, for example, a compound of formula I wherein $R_1$ is hydrogen may be reacted with an appropriate diazoalkane, or with the appropriate alkyl alcohol in the presence of an acid such as hydrochloric acid, p-toluenesulfonic acid, sulfonic ion-exchange resins and the like.

Also included in this invention are the pharmaceutically-acceptable salts of those compounds of formula I wherein $R_1$ is hydrogen. The salts are prepared by reaction of these acids with the appropriate inorganic or organic base. The salts possess the same prostaglandin antagonist activity as the parent acids when administered to an animal. Suitable pharmaceutically-acceptable cations are those derived from the alkali metals, for example, sodium, lithium and potassium, and from the alkaline earth metals, such as magnesium and calcium. Other pharmaceutically-acceptable metal ions may, however, be employed. Suitable salts also include those containing ammonium, quaternary ammonium or amine cations. Examples of suitable pharmaceutically-acceptable quaternary ammonium cations include tetramethylammonium, tetraethylammonium and the like. Examples of pharmaceutically-acceptable amine cations include those derived from primary, secondary or tertiary amines, such as methyl amine, dimethyl amine, trimethyl amine, ethyl amine and dibutyl amine. Many other suitable pharmaceutically-acceptable cations will be well known to those skilled in the art and the specific examples described above are not intended to limit the invention in any way.

The compounds of formula I are useful pharmacological and therapeutic agents. Specifically, they may be used to antagonize the action of prostaglandins of the $PGE_2$ type and consequently may be used to treat or alleviate undesirable conditions or diseases associated with an abnormal physiological excess of such prostaglandins in an animal. Such conditions include habitual abortion, diarrhea, bone resorption, sickle-cell anemia, glaucoma, fever, inflammation and pain, see Sanner, Arch. Int. Med. 133, 133 (1974). The novel compounds of this invention can be used in a variety of pharmaceutical preparations which contain the compound or pharmaceutically-acceptable salts thereof, and may be administered by a variety of routes, including orally, parenterally and topically. They may also be administered in slow release, long acting formulations.

The dosage required will vary according to the method of administration and with the species of animals to be treated and the particular result desired. The physician will, in any event, determine the particular dosage most suitable for the individual patient. When used parenterally, the compounds of formula I in the present invention may be used in sterile solutions in doses of about 0.2 to 20 mg/kg body weight of the subject to be treated. When administered orally, the compounds may be administered in the form of tablets or capsules at doses of about 2 to 200 mg/kg/day.

To prepare any of the above dosage forms, or any of the numerous other forms possible, various inert diluents, excipients or carriers may be employed. Such substances include, for example, water, ethanol, gelatins, lactose, starches, magnesium stearate, talc, vegetable oils, benzyl alcohols, gums, polyalkyline glycols, petroleum jelly, cholesterol and other known carriers for medicaments. If desired, these pharmaceutical compositions may contain auxiliary substances such as preserving agents, wetting agents, binding agents, stabilizing agents, flavoring agents, coating agents or other therapeutic agents such as antibiotics.

The prostaglandin antagonist activity of the 2,3,6-substituted-4-pyrone derivatives of formula I may be demonstrated in pharmacological tests. A suitable test for this purpose is based on the enhancement of cyclic AMP (adenosine-3',5'-monophosphate) levels in tissues due to adenyl cyclase stimulated by the action of prostaglandins of the $PGE_2$ type. An exemplification of such a test used to determine the antagonist activity of the compounds of the present invention is as follows. A BC 57/BL (Jackson Laboratories) mouse is sacrificed and the thymus gland removed and teased apart to provide thymus cells which are suspended in a culture medium. The degradation of c-AMP is blocked by addition of 4-(3-butoxy-4-methoxybenzyl)-2-imidazolidinone (Hoffman-LaRoche, Ro 20-1724), a c-AMP phosphodiesterase inhibitor. A measured dose of the compound under test is added to the suspension of cells and the suspension is incubated at 37° C. for ten minutes. A measured dose of $PGE_2$ is added to the suspension, which is then incubated for a further period of 30 minutes. The cells are then centrifuged, washed and the c-AMP extracted with ethanol. The ethanol extract is evaporated to dryness, redissolved in buffer solution and the c-AMP level determined by a radioimmunoassay, see Zimmerman et al, Anal. Biochem. 71, 79 (1976) and Steiner et al, J. Biol. Chem. 247, 1106 (1972). Comparison of the enhancement of c-AMP levels produced by $PGE_2$ alone and by $PGE_2$ together with the compound under test allow determination of the antagonist activity.

An example of the results from this test are those obtained with 2-(3-hydroxy-trans-1-octenyl)-3-(5-carboethoxypentyloxy)-4-pyrone. The initial c-AMP level of the cell culture was measured as $1.9 \pm 0.7$ picomole c-AMP/$10^7$ cells. Incubation with $10^{-5}$ M PGE$_2$ alone enhanced the level to $88 \pm 7$ picomole c-AMP/$10^7$ cells. By comparison, when the cells were incubated for ten minutes with $7 \times 10^{-5}$ M of the test compound the c-AMP level was measured at $2 \pm 0.1$ picomole c-AMP/$10^7$ cells. Following incubation for 30 minutes with $10^{-5}$ M PGE$_2$ the level was measured as $51 \pm 5$ picomole c-AMP/$10^7$ cells. Similarly, in a second experiment, after ten minutes incubation with $7 \times 10^{-6}$ M of the test compound, the c-AMP level was measured at $1.4 \pm 0.2$ picomoles c-AMP/$10^7$ cells; after 30 minutes incubation with $10^{-5}$ M PGE$_2$ the c-AMP level was measured as $69 \pm 8$ picomoles c-AMP/$10^7$ cells. Under the same test conditions $5 \times 10^{-5}$ M of the known dibenzoxazepine derivative SC-19220 (Sanner, Arch. Int. Pharmacodyn. Ther., 180, 46 (1969)) caused a 30% inhibition of c-AMP accumulation and the Fried compound, 7-oxa-13-prostynoic acid (Fried et al, Ann. New York Acad. Sci., 180, 38 (1971)) at a concentration of $10^{-4}$ M caused a 45% inhibition of the accumulation of c-AMP by PGE$_2$. Both of these compounds are well known in the art as prostaglandin antagonists.

The present invention is further illustrated by the following examples. It should be noted, however, that the invention is not limited to the specific details of these examples. Unless otherwise noted, all temperatures in the following examples are in ° C.

EXAMPLE 1

Preparation of 2-hydroxymethyl-3-(5-carboethoxypentyloxy)-4-pyrone

To a solution of 2.75 g (0.042 mole) of potassium hydroxide in 38 ml of ethanol and 10 ml of water was added 5.93 g (0.042 mole) of 2-hydroxymethyl-3-hydroxy-4-pyrone, and the resulting mixture heated to 50°. A 12.4 g (0.046 mole) portion of ethyl 6-iodohexanoate was then added and the resulting clear solution heated at reflux for 7 hr under a nitrogen atomsphere. Removal of the ethanol under reduced pressure left a residue which was dissolved in methylene chloride. The organic solution was washed successively with aqueous NaHCO$_3$ and saturated brine, was dried over magnesium sulfate, and was evaporated to afford a viscous oil. This material was chromatographed on silica gel eluting with ethyl acetate to give 6.34 g (54%) of oily product, 2-hydroxymethyl-3-(5-carboethoxypentyloxy)-4-pyrone: NMR (CDCl$_3$): δ1.22 (3H, t, J = 7Hz), 2.30 (2H, t, J = 5.5 Hz), 4.63 (2H, s), 6.35 (1H, d, J = 6 Hz), 7.73 (1H, d, J = 6 Hz).

EXAMPLE 2

Preparation of 2-formyl-3-(5-carboethoxypentyloxy)-4-pyrone

To a solution of 6.35 g (0.022 mole) of 2-hydroxymethyl-3-(5-carboethoxypentyloxy)-4-pyrone in 250 ml of acetone was added 12 g of activated manganese dioxide. The resulting suspension was stirred for 3 hr, at which time the mixture was filtered and the filtrate evaporated to an oil. The oil was triturated with hexane/ether to give the crystalline aldehyde, 2-formyl-3-(5-carboethoxypentyloxy)-4- pyrone, weighing 4.1 g (65%), m.p. 32–34.5°.

Analytical: Calcd. for $C_{14}H_{18}O_6$: C, 59.56; H, 6.42. Found: C, 59.16; H, 6.37.

EXAMPLE 3

Preparation of 2-(3-oxo-trans-1-octenyl)-3-(5-carboethoxypentyloxy)-4-pyrone To a solution, under nitrogen, of 0.224 g (4.7 mmole) of sodium hydride (50% dispersion in mineral oil) in 15 ml of dry THF was added dropwise 1.32 g (5.95 mmole) of dimethyl (2-oxoheptyl)-phosphonate. The heterogeneous mixture was stirred for 1.0 hour then a solution of 1.2 g (4.25 mmole) of 2-formyl-3-(5-carboethoxypentyloxy)-4-pyrone in 5 ml of THF was added. The mixture was stirred for 15 min then was neutralized to a pH of about 7 with glacial acetic acid. The neutralized solution was concentrated by rotary evaporation and the residue dissolved in methylene chloride. The organic solution was washed with saturated brine solution and dried over magnesium sulfate. Removal of the solvent left an oil which was purified by chromatography on silica gel using ether as the eluent. Concentration of the fractions containing product furnished 1.16 g (73%) of pure enone, 2-(3-oxo-trans-1-octenyl)-3-(5-carboethoxypentyloxy)-4-pyrone, as an oil. NMR (CDCl$_3$): δ0.88 (3H, t, J = 5 Hz); 1.22 (3H, t, J = 7 Hz), 2.26 (2H, t, J = 6.5 Hz); 2.60 (2H, t, J = 6.5 Hz); 3.85–4.31 (4H, m).

EXAMPLE 4

Preparation of 2-[(3RS)-3-hydroxy-trans-1-octenyl]-3-(5-carboethoxypentyloxy)-4-pyrone To a solution, cooled under nitrogen to −78°, of 0.200 g (0.53 mmol) of 2-(3-oxo-trans-1-octenyl)-3-(5-carboethoxypentyloxy)-4-pyrone in 2 ml of tetrahydrofuran was added dropwise keeping the internal temperature at −70° to −75°, 0.53 ml (0.53 mmole) of lithium triethylborohydride. After being stirred for an additional 30 min the cold reaction was quenched by the addition of 0.5 ml of 40% aqueous acetic acid and then partially concentrated under reduced pressure. The residue was dissolved in methylene chloride and washed successively with aqueous sodium bicarbonate and brine solution. The organic solution was dried over magnesium sulfate and evaporated to give an oil. Chromatographic purification on silica gel eluting with ether furnished 0.131 g (65%) of 2-[(3RS)-3-hydroxy-trans-1-octenyl]-3-(5-carboethoxypentyloxy)-4-pyrone. NMR (CDCl$_3$, 100 M Hz): δ0.90 (3H, t, J = 4.5 Hz), 2.33 (2H, t, J = 6 Hz), 4.13 (4H, m), 4.35 (1H, m).

EXAMPLE 5

Preparation of 8-oxo-4,8-dihydro-6-(hydroxymethyl)-2-phenyl-4H-pyrano[3,2-d]-m-dioxin A solution of 2,6-dihydroxymethyl-3-hydroxy-4-pyrone (34.4 g, 0.2 mole), benzaldehyde diethylacetal (43.2 g, 0.24 mole), and p-toluenesulfonic acid (2.4 g) in 120 ml of dimethylsulfoxide was heated at 95° for 1 hr. Benzene was then added and the mixture was heated until 1.2 l of the benzene/ethanol azetrope was collected by distillation. The cooled mixture was diluted with ethyl acetate and the resulting organic solution was washed successively with aqueous Na$_2$CO$_3$ and brine. After drying over magnesium sulfate the solvent was removed to give 28 g of crude product. Recrystallization from CH$_2$Cl$_2$/hexane afforded 23 g of pure 8-oxo-4,8-dihydro-6-(hydroxymethyl)-2-phenyl-4H-pyrano[3,2-d]-m-dioxin, m.p. 171°-172°.

Analytical: Calcd. for C$_{14}$H$_{12}$O$_5$: C, 64.61; H, 4.65 Found: C, 64.45; H, 4.74.

EXAMPLE 6

Preparation of 8-oxo-4,8-dihydro-6-(trimethylacetoxymethyl)-2-phenyl-4H-pyrano[3,2-d]-m-dioxin To a solution of 28 g (0.11 mole) of 8-oxo-4,8-dihydro-6-(hydroxymethyl)-2-phenyl-4H-pyrano[3,2-d]-m-dioxin in 125 ml of methylene chloride and 13 ml of pyridine was added 16 ml (0.13 mole) of trimethylacetyl chloride, and the mixture was stirred at 40° overnight. The mixture was then diluted with additional methylene chloride and the organic solution washed successively with 1N HCl, aqueous NaHCO$_3$ and aqueous NaCl. The dried solution was evaporated under reduced pressure to give a dark oil. Chromatography on silica gel eluting with ethyl acetate furnished the purified product, 8-oxo-4,8-dihydro-6-(trimethylacetoxymethyl)-2-phenyl-4H-pyrano[3,2-d]-m-dioxin, as an oil. Trituration with hexane gave 24.5 g (66%) of crystalline product, m.p. 110°-112°.

Analytical: Calcd. for C$_{19}$H$_{20}$O$_6$: C, 66.26, H, 5.85. Found: C, 65.77, H, 5.92.

EXAMPLE 7

Preparation of 2-hydroxymethyl-3-hydroxy-6-(trimethylacetoxymethyl)-4-pyrone

A solution of 8-oxo-4,8-dihydro-6-(trimethylacetoxymethyl-2-phenyl-4H-pyrano[3,2-d]-m-dioxin (24.5 g, 0.07 mole) in 250 ml of 65% aqueous acetic acid was heated at 70° for 3 hr. The solvents were removed in vacuo to a residue which was triturated with hexane to give 16.2 g of solid. Recrystallization from benzene furnished 14 g (78%) of pure product, 2-hydroxymethyl-3-hydroxy-6-(trimethylacetoxymethyl)-4-pyrone, m.p. 124°-125°.

Analytical: Calcd. for C$_{12}$H$_{16}$O$_6$: C, 56.24; H, 6.29 Found: C, 56.22; H, 6.33.

EXAMPLE 8

Preparation of 2-hydroxymethyl-3-(5-carboethoxypentyloxy)-6-(trimethylacetoxymethyl)-4-pyrone To a solution of 1.84 g (0.028 mole) of potassium hydroxide in 38 ml of ethanol and 10 ml of water was added 6.76 g (0.026 mole) of 2-hydroxymethyl-3-hydroxy-6-(trimethylacetoxymethyl)-4-pyrone, and the resulting mixture heated to 50°. An 8.3 g (0.03 mole) portion of ethyl 6-iodohexanoate was then added and the resulting clear solution heated at reflux for 7 hr under a nitrogen atmosphere. Removal of the ethanol under reduced pressure left a residue which was dissolved in methylene chloride. The organic solution was washed successively with aqueous NaHCO$_3$ and saturated brine, was dried over magnesium sulfate, and was evaporated to afford a viscous oil. This material was chromatographed on silica gel eluting with ethyl acetate to give 2.9 g (27%) of oily product, 2-hydroxy-3-(5-carboethoxypentyloxy)-6-(trimethylacetoxymethyl)-4-pyrone. NMR (CDCl$_3$): δ1.22 (3H, t, J = 7 Hz), 1.23 (9H, s), 2.30 (2H, t, J = 5.5 Hz), 6.32 (1H, s).

EXAMPLE 9

Preparation of 2-formyl-3-(5-carboethoxypentyloxy)-6-(trimethylacetoxymethyl)-4-pyrone To a solution of 2.3 g of 2-hydroxymethyl-3-(5-carboethoxypentyloxy)-6-(trimethylacetoxymethyl)-4-pyrone in 75 ml of acetone was added 4 g of activated manganese dioxide. The resulting suspension was stirred for 3 hr, at which time the mixture was filtered and the filtrate evaporated to an oil. The oil was chromatographed on silica gel to give the oily aldehyde, 2-formyl-3-(5-carboethoxypentyloxy)-6-(trimethylacetoxymethyl)-4-pyrone weighing 1.6 g (70%). NMR (CDCl$_3$): δ1.28 (3H, t, J = 7 Hz), 1.30 (9H, s), 2.31 (2H, t, J = 5.5 Hz), 4.17 (2H, q, J = 7 Hz), 4.48 (2H, t, J = 7Hz).

EXAMPLE 10

Preparation of 2-(3-oxo-trans-1-octenyl)-3-(5-carboethoxypentyloxy)-6-(trimethylacetoxymethyl)-4-pyrone To a solution, under nitrogen, of 0.206 g (4.3 mmole) of sodium hydride (50% dispersion in mineral oil) in 15 ml of dry THF was added dropwise 1.04 g (4.69 mmole) of dimethyl (2-oxoheptyl)-phosphonate. The heterogeneous mixture was stirred for 1.0 hour then a solution of 1.55 g (3.9 mmole) of 2-formyl-3-(5-carboethoxypentyloxy)-6-(trimethylacetoxymethyl)-4-pyrone in 5 ml of THF was added. The mixture was stirred for 15 min then was neutralized to pH 7 with glacial acetic acid. The neutralized solution was concentrated by rotary evaporation and the residue dissolved in methylene chloride. The organic solution was washed with saturated brine solution and dried over magnesium sulfate. Removal of the solvent left an oil which was purified by chromatography of silica gel using ether as the eluent. Concentration of the fractions containing product furnished 0.425 g (22%) of pure 2-(3-oxo-trans-1-octenyl)-3-(5-carboethoxypentyloxy)-6-trimethylacetoxymethyl)-4-pyrone as an oil. NMR (CDCl$_3$): δ0.88 (3H, t, J = 5 Hz); 1.25 (9H, s), 2.27 (2H, t, J = 6.5 Hz); 2.60 (2H, t, J = 6.5 Hz); 4.91 (2H, s).

EXAMPLE 11

Preparation of 2-[(3RS)-3-hydroxy-trans-1-octenyl]-3-(5-carboethoxypentyloxy)-6-(trimethylacetoxymethyl)-4-pyrone To a solution, cooled under nitrogen to −78°, of 0.715 g (1.45 mmol) of 2-(3-oxo-trans-1-octenyl)-3-(5-carboethoxypentyloxy)-6-(trimethylacetoxymethyl)-4-pyrone in 10 ml of tetrahydrofuran was added dropwise keeping the internal temperature at −70° to −75°, 1.7 ml (1.7 mmole) of lithium triethylborohydride. After being stirred for an additional 30 min the cold reaction was quenched by the addition of 5 drops of 40% aqueous acetic acid and then partially concentrated under reduced pressure. The residue was dissolved in methylene chloride and washed successively with aqueous sodium bicarbonate and brine solution. The organic solution was dried over magnesium sulfate and evaporated to give an oil. Chromatographic purification on silica gel eluting with ether furnished 0.290 g (40%) of 2-[(3RS)-3-hydroxy-trans-1-octenyl]-3-(5-carboethoxypentyloxy)-6-(trimethylacetoxymethyl)-4-pyrone. NMR (CDCl$_3$): δ0.90 (3H, t, J = 4.5 Hz), 2.31 (2H, t, J = 6 Hz), 4.88 (2H, s).

EXAMPLE 12

Preparation of 2-[(3RS)-3-hydroxy-trans-1-octenyl]-3-(5-carbomethoxypentyloxy)-6-hydroxymethyl-4-pyrone To a solution of 2-[(3RS)-3-hydroxy-trans-1-octenyl]-5-(carboethoxypentyloxy)-6-(trimethylacetoxymethyl)-4-pyrone (290 mg, 0.6 mmole) in 5 ml of dry methanol was added 167 mg (1.2 mmole) of anhydrous potassium carbonate, and the suspension stirred for 30 min at room temperature. Excess methylene chloride was added, the resulting mixture was filtered, and the filtrate was evaporated under reduced pressure. The residue was chromatographed on silica gel eluting with ethyl acetate to give 133 mg (55%) of oily product, 2-[(3RS)-3-hydroxy-trans-1-octenyl]-3-(5-carbomethoxypentyloxy)-6-hydroxymethyl-4-pyrone. NMR (CDCl$_3$, 100 M Hz) δ0.88 (3H, t, J = 4.5 Hz), 2.33 (2H, t, J = 6 Hz), 3.68 (3H, s), 4.46 (2H, s).

EXAMPLE 13

Preparation of 2-(3-oxo-5-phenyl-trans-1-pentenyl)-3-(5-carboethoxypentyloxy)-4-pyrone To a solution, under nitrogen, of 0.187 g (3.9 mmole) of sodium hydride (50% dispersion in mineral oil) in 10 ml of dry THF was added dropwise 1.2 g (4.95 mmole) of dimethyl (2-oxo-4-phenylbutyl)-phosphonate. The heterogeneous mixture was stirred for 1.0 hour then a solution of 1.0 g (3.54 mmole) of 2-formyl-3-(5-carboethoxypentyloxy)-4-pyrone, prepared by the procedure of Examples 1 and 2, in 5 ml of THF was added. The mixture was stirred for 15 min then was neutralized to pH 7 with glacial acetic acid. The neutralized solution was concentrated by rotary evaporation and the residue dissolved in methylene chloride. The organic solution was washed with saturated brine solution and dried over magnesium sulfate. Removal of the solvent left an oil which was purified by chromatography on silica gel using ether as the eluent. Concentration of the fractions containing product furnished 0.90 g (64%) of pure 2-(3-oxo-5-phenyl-trans-1-pentenyl)-3-(5-carboethoxypentyloxy)-4-pyrone, m.p. 38.5–40°. NMR (CDCl$_3$): δ1.26 (3H, t, J = 7 Hz); 2.35 (2H, t, J = 6.5 Hz).

Analytical: Calcd. for C$_{24}$H$_{28}$O$_6$: C, 69.90; H, 6.84
Found: C, 69.90; H, 6.78

EXAMPLE 14

Preparation of 2-[(3RS)-3-hydroxy-5-phenyl-trans-1-pentenyl]-3-(5-carboethoxypentyloxy)-4-pyrone To a solution, cooled under nitrogen to −78°, of 0.823 g (1.99 mmol) of 2-(3-oxo-5-phenyl-trans-1-pentenyl)-3-(5-carboethoxypentyloxy)-4-pyrone in 4 ml of tetrahydrofuran was added dropwise keeping the internal temperature at −70° to −75°, 1.89 ml (1.89 mmole) of lithium triethylborohydride. After being stirred for an additional 30 min the cold reaction was quenched by the addition of 2.0 ml of 40% aqueous acetic acid and then partially concentrated under reduced pressure. The residue was dissolved in methylene chloride and washed successively with aqueous sodium bicarbonate and brine solution. The organic solution was dried over magnesium sulfate and evaporated to give an oil. Chromatographic purification on silica gel eluting with ether furnished 0.233 g (28%) of 2-[(3RS)-3-hydroxy-5-phenyl-trans-1-pentenyl]-3-(5-carboethoxypentyloxy)-4-pyrone. NMR (CDCl$_3$, 100 M Hz): δ1.26 (3H, t, J = 7.0 Hz), 2.32 (2H, t, J = 6 Hz).

EXAMPLE 15

Preparation of 2-hydroxymethyl-6-methyl-3-(5-carboethoxypentyloxy)-4-pyrone

To a solution of 2.00 g (0.0304 mole) of potassium hydroxide in 33 ml of ethanol and 5 ml of water was added 4.75 g (0.0304 mole) of 2-hydroxymethyl-3-hydroxy-6-methyl-4-pyrone, and the resulting mixture heated to 50°. A 7.8 g (0.029 mole) portion of ethyl 6-iodohexanoate was then added and the resulting clear solution heated at reflux for 7 hr under a nitrogen atmosphere. Removal of the ethanol under reduced pressure left a residue which was dissolved in methylene chloride. The organic solution was washed successively with aqueous NaHCO$_3$ and saturated brine, was dried over magnesium sulfate, and was evaporated to afford a viscous oil. This material was chromatographed on silica gel eluting with ethyl acetate to give 5.4 g (60%) of oily product, 2-hydroxymethyl-6-methyl-3-(5-carboethoxypentyloxy)-4-pyrone. NMR (CDCl$_3$): δ1.22 (3H, t, J = 7 Hz), 2.26 (3H, s); 4.61 (2H, m); 6.17 (1H, s).

EXAMPLE 16

Preparation of 2-formyl-6-methyl-3-(5-carboethoxypentyloxy)-4-pyrone

To a solution of 4.25 g of 2-hydroxymethyl-6-methyl-3-(5-carboethoxypentyloxy)-4-pyrone in 110 ml of acetonitrile was added 12 g of activated manganese dioxide. The resulting suspension was stirred for 3 hr, at which time the mixture was filtered and the filtrate evaporated to an oil, 2-formyl-6-methyl-3-(5-carboethoxypentyloxy)-4-pyrone, weighing 4.0 g (94%). NMR (CDCl$_3$): δ1.23 (3H, t, J = 7 Hz), 2.36 (3H, s), 6.32 (1H, s).

EXAMPLE 17

Preparation of 2-(3-oxo-trans-1-octenyl)-6-methyl-3-(5-carboethoxypentyloxy)-4-pyrone To a solution, under nitrogen, of 0.561 g (11.6 mmole) of sodium hydride (50% dispersion in mineral oil) in 20 ml of dry THF was added dropwise 3.07 g (13.8 mmole) of dimethyl (2-oxoheptyl)-phosphate. The heterogeneous mixture was stirred for 1.0 hour then a solution of 3.15 g (10.6 mmole) of the aldehyde in 10 ml of THF was added. The mixture was stirred for 15 min then was neutralized to a pH of about 7 with glacial acetic acid. The neutralized solution was concentrated by rotary evaporation and the residue dissolved in methylene chloride. The organic solution was washed with saturated brine solution and dried over magnesium sulfate. Removal of the solvent left an oil which was purified by chromatography on silica gel using ether as the eluent. Concentration of the fractions containing product furnished 3.1 g (75%) of pure 2-(3-oxo-trans-1-octenyl)-6-methyl-3-(5-carboethoxypentyloxy)-4-pyrone as an oil. NMR (CDCl$_3$): δ0.88 (3H, t, J = 5 Hz); 1.22 (3H, t, J = 7 Hz), 2.32 (3H, s); 2.70 (2H, t, J = 7.0 Hz).

EXAMPLE 18

Preparation of 2-[(3RS)-3-hydroxy-trans-1-octenyl]-6-methyl-3-(5-carboethoxypentyloxy)-4-pyrone To a solution, cooled under nitrogen to −78°, of 1.8 g (4.6 mmol) of 2-(3-oxo-trans-1-octenyl)-6-methyl-3-(5-carboethoxypentyloxy)-4-pyrone in 20 ml of tetrahydrofuran was added dropwise keeping the internal temperature at −70° to −75°, 30 ml (4.6 mmole) of lithium triethylborohydride. After being stirred for an additional 30 min the cold reaction was quenched by the addition of 3.0 ml of 40% aqueous acetic acid and then partially concentrated under reduced pressure. The residue was dissolved in methylene chloride and washed successively with aqueous sodium bicarbonate and brine solution. The organic solution was dried over magnesium sulfate and evaporated to give an oil. Chromatographic purification on silica gel eluting with ether furnished 0.5 g (26%) of 2-[(3RS)-3-hydroxy-trans-1-octenyl]-6-methyl-3-(5-carboethoxypentyloxy)-4-pyrone. NMR (CDCl$_3$, 100 M Hz): δ0.90 (3H, t, J = 4.5 Hz), 2.33 (3H, s).

EXAMPLE 19

The aldehydes prepared in Examples 1 and 2, and Examples 5 through 9, and other 6-substituted analogs thereof, may be reacted with other dimethyl ketophosphonates to form products which may be further reacted by the procedures of Example 4 and Examples 11 through 14 to form compounds of formula I having various 2-substituent side chains, as follows:

| Ketophosphonate | | 2-Substituent in Product | |
|---|---|---|---|
| | | n | Y |
| dimethyl | (2-oxobutyl)-phosphonate | 1 | Methyl |
| dimethyl | (2-oxohexyl)-phosphonate | 3 | Methyl |
| dimethyl | (2-oxo-3-phenyl-propyl)-phosphonate | 1 | Phenyl |
| dimethyl | (2-oxo-5-phenyl-pentyl)-phosphonate | 3 | Phenyl |
| dimethyl | (2-oxo-6-phenyl-hexyl)-phosphonate | 4 | Phenyl |
| dimethyl | (2-oxo-5-(p-chlorophenyl)-pentyl)-phosphonate | 3 | p-chlorophenyl |
| dimethyl | (2-oxo-4-(m-methylphenyl)-butyl)-phosphonate | 2 | m-methylphenyl |
| dimethyl | (2-oxo-3-(p-methoxyphenyl)-propyl)-phosphonate | 1 | p-methoxyphenyl |

What is claimed is:

1. A compound of the formula

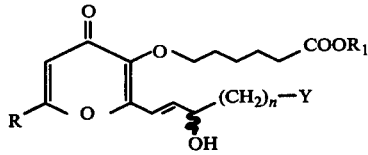

wherein
   $R_1$ is hydrogen or alkyl of 1 to 6 carbon atoms;
   R is selected from hydrogen, methyl, ethyl, n-propyl and 1-hydroxyalkyl, wherein said alkyl is methyl, ethyl and n-propyl;
   Y is selected from methyl, phenyl and monosubstituted phenyl, wherein said substituent is methyl, methoxy, chloro or fluoro;
   n is an integer from 1 to 4;
   and the pharmaceutically acceptable salts of said compounds wherein $R_1$ is hydrogen.

2. A compound of claim 1 wherein R is hydrogen, methyl or hydroxymethyl.

3. A compound of claim 1 wherein Y is methyl or phenyl.

4. A compound of claim 2 wherein R is hydrogen.

5. A compound of claim 4 wherein $R_1$ is ethyl, n is 4 and Y is methyl.

6. A compound of claim 4 wherein $R_1$ is ethyl, n is 2 and Y is phenyl.

7. A compound of claim 2 wherein R is methyl.

8. A compound of claim 7 wherein $R_1$ is ethyl, n is 4 and Y is methyl.

9. A compound of claim 2 wherein R is hydroxymethyl.

10. A compound of claim 9 wherein $R_1$ is methyl, n is 4 and Y is methyl.

11. A compound of claim 1 wherein Y is methyl.

12. A compound of claim 1 when Y is selected from phenyl and monosubstituted phenyl, wherein said substituent is methyl, methoxy, chloro or fluoro.

* * * * *